United States Patent [19]

Gore, Jr.

[11] Patent Number: 4,662,367
[45] Date of Patent: May 5, 1987

[54] TRACHEA SUCTION TUBE
[75] Inventor: Mack Gore, Jr., Brownsville, Tex.
[73] Assignee: Leonard Olguin, Brownsville, Tex.
[21] Appl. No.: 826,739
[22] Filed: Feb. 6, 1986
[51] Int. Cl.[4] .......................................... A61M 16/04
[52] U.S. Cl. .................................. 128/202.28; 604/35; 604/73; 604/131; 604/268; 604/275; 604/319; 604/328
[58] Field of Search ..................... 128/202.28; 604/30, 604/35, 73, 118, 131, 149, 268, 275, 276, 319, 328, 902

[56] References Cited
U.S. PATENT DOCUMENTS

| | | | |
|---|---|---|---|
| 3,057,347 | 12/1959 | McGee | 128/202.28 |
| 3,297,027 | 1/1967 | Rusch | 128/202.28 |
| 3,638,655 | 2/1972 | Doherty | 128/207.15 |
| 3,683,908 | 8/1972 | Michael | 128/207.15 |
| 4,231,364 | 11/1980 | Speshyock | 128/207.14 |
| 4,233,984 | 11/1980 | Walling | 128/207.14 |
| 4,478,215 | 10/1984 | Hanlon | 128/207.14 |
| 4,535,765 | 8/1985 | Paoluccio | 128/203.11 |

Primary Examiner—Kyle L. Howell
Assistant Examiner—Randy Citriu
Attorney, Agent, or Firm—Crutsinger & Booth

[57] ABSTRACT

Apparatus to remove an obstruction from a trachea airway comprising: a mouthpiece having a sealing lip surface extending around the periphery of a passageway extending therethrough the sealing surface being adapted to sealingly engage larynx surfaces to position a first end of said passageway in fluid communication with a trachea airway. A filter absorbs liquid flowing through the passageway to permit reduction of air pressure in the mouthpiece by suction of lifesaving personnel to draw an obstruction from the trachea airway of a patient to the mouthpiece.

10 Claims, 4 Drawing Figures

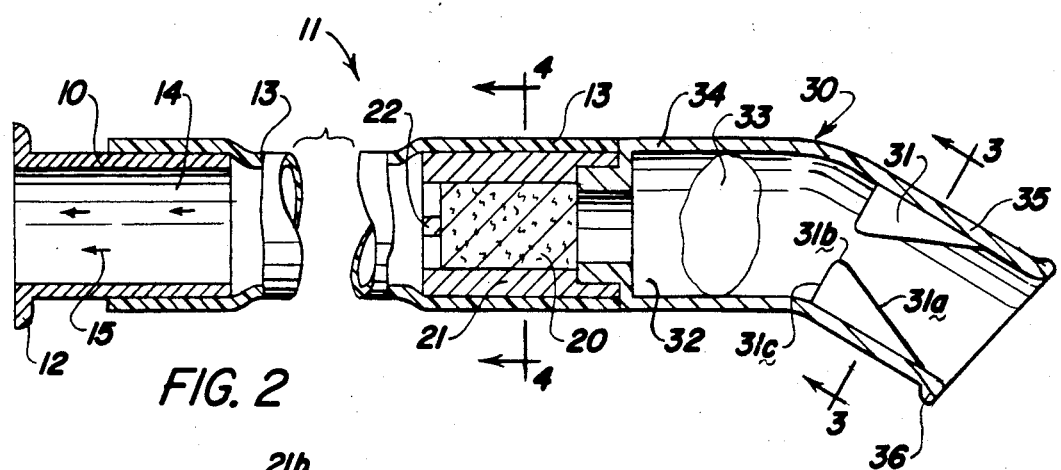
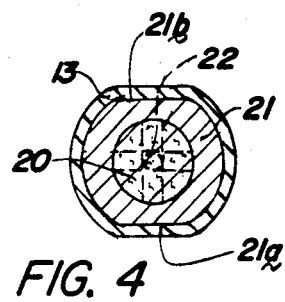
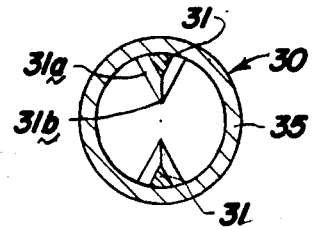
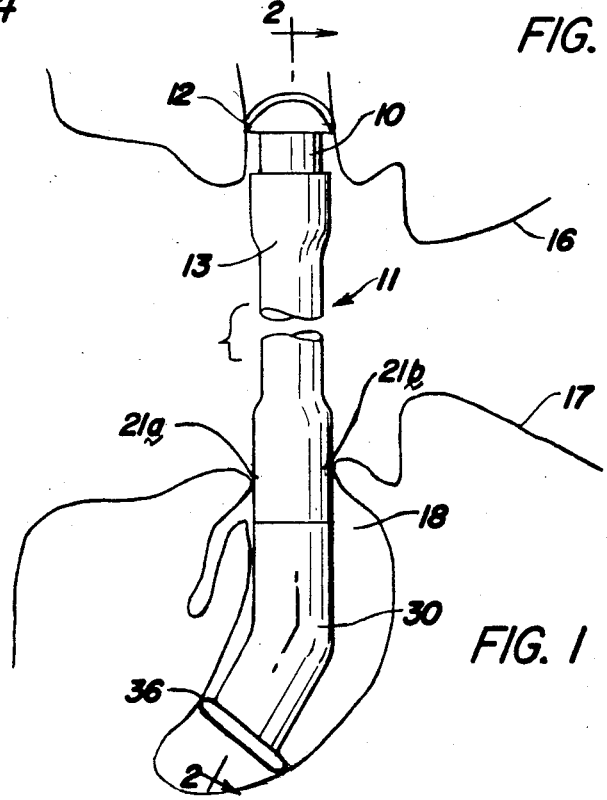

TRACHEA SUCTION TUBE

BACKGROUND OF INVENTION

The invention relates to devices to facilitate lifesaving and particularly to victims who are choking. Choking is defined as the stopping of breath due to blockage by an obstruction. The obstruction would most likely be lodged in the trachea which is the tube extending from the larynx to the bronchi, by which air is carried to and from the lungs.

Heretofore, there has been no device to remove an obstruction from a trachea airway using a filter which permits passage of air while blocking liquid extracted from the throat of the victim as a result of suction applied to the device. A Texas Department of Health Resources pamphlet indicates that first aid measures now used for lifesaving of choking victims consists of: forcing a cough, bending a person over and giving them a hard slap between the shoulder blades, attempting to remove obstruction with the fingers, cutting a hole through the neck into the windpipe with a sharp object to create an emergency airway, and the best known method called the Heimlich Maneuver. This maneuver involves an abrupt upward squeeze of the choking victim's upper abdomen to expel the obstruction blocking the air passage. Using these above lifesaving measures, difficulties can occur such as: fear of being bitten, fear of germ transmission, and the fear of disease transmission such as AIDS or mononucleosis.

According to reports of the National Safety Council, foreign body obstruction of the airway ranks sixth as a cause of accidental death in the United States and accounts for approximately 3,000 to 4,000 deaths per year. A victim has approximately three minutes before blackout occurs and approximately five minutes before death may occur. It is said that approximately three out of five victims do not get to the hospital in time; therefore, a device is needed so that "on the spot" lifesaving can save numerous people from death by suffocation.

SUMMARY OF INVENTION

The invention described herein is an apparatus for removal of an obstruction from a trachea airway. The apparatus comprises a mouthpiece having a passageway extending herethrough, a sealing lip surface on the mouthpiece extending around the periphery of the passageway that engages the trachea airway surfaces to form a seal for suction, an absorbent fiber adjacent a second end of the passageway to absorb liquid flowing through a said passageway, and a second mouthpiece associated with the filter to permit reduction of air pressure in the mouthpiece to draw an obstruction from the trachea airway to the mouthpiece. The apparatus incorporates a resilient trap in the passageway intermediate opposite ends of said passageway adapted to permit passage of solid material into said passageway and to block passage of solid material from said passageway. The trap comprises a plurality of deformable flutes extending into said passageway, a guide surface and a blocking surface being formed on each flute such that the blocking surfaces are stiffer than the guide surfaces to trap solid material in said passeway.

It is an object of the invention to provide a safe, sanitary, an easy to use device so that an untrained individual can give lifesaving help for a choking victim.

BRIEF DESCRIPTION OF THE DRAWINGS

The invention will be better understood by reference to the accompanying drawings in which:

FIG. 1 is a side elevational view of the apparatus in accordance with the invention;

FIG. 2 is an enlarged cross-sectional view taken along line 2—2 of FIG. 1;

FIG. 3 is a cross-sectional view taken along line 3—3 of FIG. 2; and

FIG. 4 is a cross-sectional view taken along line 4—4 of FIG. 2.

DESCRIPTION OF THE PREFERRED EMBODIMENT

Referring to FIG. 1, the trachea suction tube 11 is illustrated along with the person 17 being saved and the person 16 performing the lifesaving procedures. It will be understood that the term "lifesaver" is used herein to refer to the person who is helping a patient or victim 17.

The trachea suction tube 11 comprises a mouthpiece 10 for a lifesaver 16 which is connected by a flexible tube 13 and a filter cup 21, holding a fibrous absorbent material 20, to a mouthpiece cup 30 for a victim 17.

Lifesaver mouthpiece 10 is produced from a rigid material, such as plastic or metal, so that the lifesaver 16 can clamp the mouthpiece 10 between his teeth. A mouthpiece ring 12, extending around the periphery of the mouthpiece 10, allows the lifesaver 16 to easily grasp mouthpiece 10 between his teeth freeing the lifesaver's hands to perform any other lifesaving measures that may be required. As will be hereinafter more fully explained, mouthpiece 10 has a passage 14 extending longitudinally.

Mouthpiece 10 may assume any suitable configuration. However, the mouthpiece is preferably a tubular member adapted to be grasped between the teeth of lifesaving personnel and may have an elliptical-shaped cross-section to provide a cross-sectional area of passage 14 for drawing air as illustrated by arrow 15 through mouthpiece 10. Ring 12 may be substantially flat but is preferably curved to approximately the curvature of the front teeth of lifesaving personnel such that application of force by the tongue of the person using the device will stabilize the mouthpiece to facilitate positioning the lips around the outer surface of the mouthpiece 10 in sealing engagement with the outer surface of the mouthpiece such that a sucking action in the mouth of the lifesaver will draw air through passage 14.

The mouthpiece 10 is connected to the filter cup 21 by a flexible tube 13. This tube 13 is flexible to permit operation by the lifesaver 16 at various angles and positions relative to the mouth 18 of victim 17. An important feature of the flexible tube 13 is that it is deformable but has sufficient stiffness to prevent collapsing under reduced pressure.

The filter cup 21 is preferably made of the same material as the mouthpiece 10 so that the filter cup will not be damaged by involuntary biting by the victim 17. One end of filter cup 21 is provided with a web 22 functioning as a filter stopper to hold the fibrous absorbent material 20 in place while allowing substantially unobstructed flow of air. The fibrous absorbent material or filter 20 is made from fibers similar to that of cigarette filter material packed to absorb liquids that may be expelled from the victim 17 during the lifesaving procedure. The fiber of filter 20 cannot be too tightly packed so that air can be removed by the lifesaver 16. Also, the filter must absorb small amounts of liquids but still allow air to pass through with relative ease. A victim's mouthpiece cup 30 is connected to the fiber cup 21 on the opposite end from web 22.

The mouthpiece cup 30 is made from a soft deformible plastic material to prevent injury to the throat of the patient or victim 17 but has sufficient rigidity so that it will not collapse when suction force is applied. The mouthpiece cup 30 may be fitted with interchangeable mouthpiece cups consisting of: adult, medium, or infant sizes. The interchangeable mouthpiece cups 30 are disposable which minimizes the sanitation requirements and the transmission of diseases.

The proximal end 34 of the mouthpiece cup 30 has a cavity 32 where airway obstruction 33 is trapped during suction by the lifesaver 16. The diameter of the mouthpiece cup 30 should be approximately the size of a grape or marble. The distal end 35 of the mouthpiece cup 30 is deflected at an angle of approximately 30° relative to the proximal end 34 and has a plurality of flutes 31 that prevent the removed obstruction 33 from being blown or sucked back into the victim's 17 airway. The distal end lip 36, formed around the periphery of the mouthpiece cup 30, is adapted to sealingly engage with the larynx surfaces to form a seal.

Symptoms for a choking victim 17 consist of: victim's inability to speak or breathe, the victim being pale or even turning bluish, panic, or the most widely known universal signal is the victim grasping at his or her neck. When any or all of these symptoms are recognized, the lifesaver 16 must quickly take control of the situation. The lifesaver 16 must put the trachea suction tube 11 into the victim's mouth and carefully push the device down his throat. The lip 36 around the periphery of the distal end 35 of the mouthpiece cup 30 forms a seal across the trachea of the victim.

The lifesaver 16 grasps the lifesaver's mouthpiece 10 between his teeth and is able to remove the obstruction 33 from the victim 17. The obstruction 33 is removed due to the suction of air that creates a vacuum throughout the air tight trachea suction tube device 11 by the lifesaver 16. Air 15 can be pulled or sucked through the tubular mouthpiece 10, tube 13, filter cup 21, and mouthpiece cup 30, with relative ease. The fibrous absorbent material 20 as described earlier also allows air to be sucked through the trachea suction tube device 11 by the lifesaver 16 with relative ease.

The obstruction 33 is sucked up into the mouthpiece cup 30 over the flutes 31 into the cavity 32. As the obstruction 33 is being sucked from the victim 17, liquid may be sucked into the trachea suction tube device. And this liquid is trapped inside the absorbent filter 20.

Flutes 31 are preferably constructed of a deformible material and are provided with converging guide surfaces 31a which terminate at an apex 31b and intersect with blocking surfaces 31c which extend generally radially of passage 32 through mouthpiece 30. The angle of inclination of guide surfaces 31a relative to the angle of inclination of blocking surfaces 31c with respect to the axis of passage 32 causes flutes 31 to be more readily deformed by an object moving into passage 32 than by an object moving out of passage 32. The flutes 31 are formed to keep the obstruction 33 from being blown back into the victim's 17 trachea or sucked back into the victim's 17 trachea by the victim himself. The obstruction 33 is trapped inside the cavity 32 and the trachea suction tube device 11 is pulled carefully from the victim 17. The mouthpiece cup 30 with the obstruction 33 and the filter 20 can be discarded.

From the foregoing it should be readily apparent that sealing lip 36 on mouthpiece 30 is adapted to sealingly engage surfaces of the larynx to position a first end of passageway 32 in fluid communication with the trachea airway of the patient. The absorbent filter adjacent the second end of the passageway 32 through mouthpiece 30 absorbs liquid flowing through passageway 32 so that the liquid will not be drawn into the mouth of the lifesaver 16 as suction force is applied to reduce air pressure in the mouthpiece. Resilient flutes 31 in passageway 32, due to the shape and configuration of guide surfaces 31a and blocking surfaces 31c, permit passage of solid material 33 into the passageway while blocking passage of the solid material 33 from the passageway. Flexible tube 13 permits adjustment of the position of mouthpiece 10 used by the lifesaver relative to the position of mouthpiece 30 which is inserted into the throat of the victim.

Tube 13 is preferably approximately ten inches long to permit observation of reactions of the victim by the lifesaver. As best illustrated in FIG. 4 of the drawing, upper and lower outer surfaces 21a and 21b of filter cup 21 preferably are flattened to visually indicate to the lifesaver how the mouthpiece 30 is oriented. If gripped between the teeth of the victim, flat surfaces 21a and 21b will rotate the mouthpiece 30 to the desired orientation.

It should be readily apparent that the apparatus to remove an obstruction from a trachea air passageway hereinbefore described can be manipulated by untrained personnel.

What is claimed is:

1. Apparatus to remove an obstruction from a trachea airway comprising: a mouthpiece having a proximal end, a distal end and a passageway extending therethrough; a sealing lip extending radially outwardly around the distal end of said mountedpiece said sealing lip having sealing surface means shaped to sealingly engage laryngal surfaces to seal the distal end of said mouthpiece to the interior of the larynx, thereby providing a continuous fluid communication between said passageway and the tracheal airway; absorbent filter means adjacent the proximal end of said passageway, said filter means being adapted to absorb liquid flowing through said passageway; and means associated with said proximal end to permit reduction of air pressure in said mouthpiece to draw an obstruction from the trachea airway to the mouthpiece.

2. Apparatus to remove an obstruction from a trachea airway according to claim 1, with the addition of: resilient means in said passageway intermediate opposite ends of said passageway, said resilient means being adapted to permit passage of solid material into said passageway and to block passage of said material from said passageway.

3. Apparatus to remove an obstruction from a trachea airway according to claim 2, said resilient means comprising: a plurality of deformable flutes extending into said passageway, a guide surface and a blocking surface on each of said flutes, said blocking surfaces being stiffer than said guide surfaces to trap solid material in said passageway.

4. Apparatus to remove an obstruction from a trachea airway according to claim 1, said mouthpiece having a distal end and a proximal end, said distal end being deflected relative to said proximal end.

5. Apparatus to remove an obstruction from a trachea airway according to claim 4, said distal end being deflected at an angle of approximately 30°.

6. Apparatus to remove an obstruction from a trachea airway according to claim 5 with the addition of a plurality of resilient flutes extending into said passageway in the distal end of said mouthpiece; inclined guide surfaces on each of said flutes; blocking surfaces on each of said flutes, said guide surfaces and said blocking surfaces intersecting at an apex such that said flutes are readily deformable by an object moving from the distal end of said mouthpiece toward said proximal end.

7. Apparatus to remove an obstruction from a trachea airway according to claim 1, said means associated with said filter means to permit reduction of air pressure in said mouthpiece comprising a deformable tube; means connecting said deformable tube to said filter means; and a second mouthpiece secured to said deformable tube.

8. Apparatus to remove an obstruction from a trachea airway comprising: a first mouthpiece having a proximal end and a distal end, said distal end being adapted to be urged into sealing engagement with larynx surfaces of a person having a blocked trachea airway, said first mouthpiece having a passageway extending therethrough; a hollow deformable tube secured to the proximal end of said first mouthpiece, said tube having a passage extending longitudinally thereof; and filter means associated with the passageway through said first mouthpiece and the passage through said tube to absorb liquid flowing therethrough while permitting passage of air.

9. Apparatus to remove an obstruction from a trachea airway according to claim 8 with the addition of a second mouthpiece secured to said deformable tube and spaced from said first mouthpiece; said second mouthpiece including an outwardly extending flange curved to have a radius of curvature such that it will lie adjacent to the inner surfaces of human teeth, said second mouthpiece being sufficiently rigid to be gripped between human teeth for supporting said tube and said second mouthpiece.

10. Apparatus to remove an obstruction from a trachea airway according to claim 8 with the addition of a reference surface adjacent the proximal end of said first mouthpiece to facilitate orientation of said first mouthpiece relative to the trachea of the victim.

* * * * *

UNITED STATES PATENT AND TRADEMARK OFFICE
CERTIFICATE OF CORRECTION

PATENT NO. : 4,662,367
DATED      : May 5, 1987
INVENTOR(S) : Mack Gore, Jr.

It is certified that error appears in the above-identified patent and that said Letters Patent is hereby corrected as shown below:

Column 4, line 39, change "mountedpiece" to

-- mouthpiece --

Signed and Sealed this

Eighth Day of September, 1987

Attest:

DONALD J. QUIGG

*Attesting Officer*      *Commissioner of Patents and Trademarks*